US00PP08960P

United States Patent [19]

Polys

[11] Patent Number: Plant 8,960

[45] Date of Patent: Oct. 25, 1994

[54] CHRYSANTHEMUM PLANT NAMED WHITE ROCHELLE

[75] Inventor: Susan M. Polys, Salinas, Calif.

[73] Assignee: Yoder Brothers, Inc., Chualar, Calif.

[21] Appl. No.: 62,258

[22] Filed: May 17, 1993

[51] Int. Cl.[5] ..... A01H 5/00

[52] U.S. Cl. ..... Plt./82.1

[58] Field of Search ..... Plt. 82.1, 74.1

[56] References Cited

U.S. PATENT DOCUMENTS 4,616,099 10/1986 Sparkes ..... 47/58

OTHER PUBLICATIONS

Chan, 1966, "Chrysanthemum and rose mutations, induced by X-rays", Am. Soc. Hort. Sci. Proc., pp. 613–620.

Broertjes, 1966, "Mutation breeding of Chrysanthemums", Euphytica, 15:156–162.

Dowick, et al., 1966, "The induction of mutations in Chrysanthemum using X- and gamma radiation", Euphytica, 15:204–210.

Broertjes, et al., 1980, "A mutant of a mutant of a . . . Irradiation of progressive radiation-induced mutants in a mutation breeding program with *Chrysanthemum morifolium*", Euphytica, 29:526–530.

Gosling, ed., 1979, "The Chrysanthemum Manual–6th edition", The National Chrysanthemum Society, London, Essex Telegraph Press, Ltd., pp. 329–336.

Broertjes, et al., 1978, "Application of Mutation Breeding Methods in the Improvement of Vegetatively Propagated Crops", Elsevier Sci. Pub. Co., New York, pp. 162–175.

Searle, et al., 1968, "Chrysanthemums the Year Round", Blanford Press, London, pp. 27–29, 320–327.

*Primary Examiner*—Howard J. Locker

*Attorney, Agent, or Firm*—Foley & Lardner

[57] ABSTRACT

A Chrysanthemum plant named White Rochelle particularly characterized by its flat capitulum form; spooned daisy capitulum type; white ray floret color; diameter across face of capitulum of 38 to 44 mm when fully opened, when grown as a pinched spray pot mum; very floriferous, with excellent display of many small flowers; photoperiodic flowering response of 50 to 53 days after start of short days; plant height, with 21 to 23 long days after sticking unrooted cuttings, and with 0 to 1 applications of 2500 ppm B-9 SP, ranges from 20 to 28 cm when grown as a pinched pot mum with 4 cuttings in a 15 cm pot; branching pattern is spreading and prolific, each plant having 5 to 7 laterals after pinch; and recommended as a spray pot mum.

1 Drawing Sheet

The present invention comprises a new and distinct cultivar of Chrysanthemum, botanically known as *Dendranthema grandiflora,* and referred to by the cultivar name White Rochelle.

White Rochelle, identified as 6834 (86-667A-05) is a product of a mutation induction program. The new cultivar was discovered and selected by Susan M. Polys on Jul. 10, 1991, in a controlled environment in Salinas, Calif., as one flowering plant within a flowering block established as rooted cuttings from stock plants which had been exposed as unrooted cuttings to an X-ray source of 2000 rads in Fort Myers, Fla., on Mar. 6, 1991. The irradiated parent was the cultivar identified as Rochelle, disclosed in U.S. Plant Pat. No. 7,768, and described as a spray pot mum with a flat capitulum form; a spooned daisy capitulum type; a purple ray floret color; diameter across face of capitulum of 38 to 44 mm when fully opened; flowering response period of 44 to 54 days after start of short days; plant height of 15 to 25 cm with 0 to 2 applications of 2500 ppm B-9 SP when grown as a pinched pot mum in a 15 cm pot, with 15 to 25 long days prior to short days; and spreading and prolific branching pattern, with 4 to 7 laterals after pinch.

The irradiation program resulting in White Rochelle had as its primary objective the expansion of the color range of Rochelle, while retaining all other traits of Rochelle. The irradiation program comprised irradiating cuttings of the parent cultivar at irradiation levels of 1500, 1750 and 2000 rads. A total of 1552 cuttings harvested from a total of 225 irradiated plants were planted on May 13, 1991, May 6, 1991 and May 6, 1991, respectively. Of these, 5 initial selections were made, which selections were then revegetated and reflowered. Three consecutive flowerings resulted in discarding 4 of the original 5 selections on Mar. 19, 1992. One selection was retained and reflowered again, ultimately resulting in the decision to introduce this remaining selection as White Rochelle.

The first act of asexual reproduction of White Rochelle was accomplished when vegetative cuttings were taken from the initial selection in September 1991 in a controlled environment in Salinas, Calif., by technicians working under supervision of Susan M. Polys.

Horticultural examination of controlled flowerings of successive plantings has shown that the unique combination of characteristics as herein disclosed for White Rochelle are firmly fixed and are retained through successive generations of asexual reproduction.

White Rochelle has not been observed under all possible environmental conditions. The phenotype may vary significantly with variations in environment such as temperature, light intensity and daylength, without, however, any variance in genotype.

The following observations, measurements and comparisons describe plants grown in Salinas, Calif., under greenhouse conditions which approximate those generally used in commercial greenhouse practice.

The following traits have been repeatedly observed and are determined to be basic characteristics of White Rochelle, which, in combination, distinguish this Chrysanthemum as a new and distinct cultivar:

1. Flat capitulum form.
2. Spooned daisy capitulum type.
3. White ray floret color.
4. Diameter across face of capitulum of 38 to 44 mm when fully opened, when grown as a pinched spray pot mum.
5. Very floriferous, with excellent display of many small flowers.
6. Photoperiodic flowering response of 50 to 53 days after start of short days.
7. Plant height, with 21 to 23 long days after sticking unrooted cuttings and with 0 to 1 applications of 2500 ppm B-9 SP, ranges from 20 to 28 cm when grown as a pinched pot mum with 4 cuttings in a 15 cm pot.
8. Branching pattern is spreading and prolific, each plant having 5 to 7 laterals after pinch.
9. Recommended as a spray pot mum.

The accompanying photographic drawing comprises a front perspective view of a potted mum of White Rochelle, with 4 cuttings in a 15 cm pot. The colors are as nearly true as possible with illustrations of this type.

Of the commercial cultivars known to the inventor, the most similar in comparison to White Rochelle is the parent cultivar Rochelle. All traits of White Rochelle are similar to those of Rochelle, except for the ray floret color, the plant height and the flowering response to short days. The ray floret color of White Rochelle is clear white, while the ray floret color of Rochelle is described as purple. White Rochelle has been 3 cm taller and up to 3 days slower in flowering response time when compared with Rochelle in side by side flowering trails. The range of measurements of Rochelle is much wider than the range of measurements of White Rochelle, based on the fact that Rochelle has been tested for a longer period of time than White Rochelle at the time of the application.

In the following description color references are made to the Royal Horticultural Society Colour Chart. The color values were determined on plant material grown as a pinched spray pot mum in Salinas, Calif., on Oct. 23, 1992. The clear white ray floret color of White Rochelle is not represented on the RHS Colour Chart.

Classification:

*Botanical.*—*Dendranthema grandiflora* cv. White Rochelle.

*Commercial.*—Flat spooned daisy spray pot mum.

INFLORESCENCE

A. Capitulum:

*Form.*—Flat spooned daisy spray pot mum.

*Type.*—Spooned daisy.

*Diameter across face.*—38 to 44 mm when fully opened.

B. Corolla of ray florets:

*Color (general tonality from a distance of three meters).*—Clear white.

*Color (upper surface).*—Clear white.

*Color (under surface).*—Clear white.

*Shape.*—Irregular flower form: Spoons and tubes of different length. Most spoons are indented. Tubes are straight.

C. Corolla of disc florets:

*Color (mature).*—14A.

*Color (immature).*—144A to 144B.

D. Reproductive organs:

*Androecium.*—Present on disc florets only; no to very scant pollen.

*Gynoecium.*—Present on both ray and disc florets.

PLANT

A. General appearance:

*Height.*—20 to 28 cm when grown as a pinched pot mum with 21 to 23 long days prior to start of short days, with 0 to 1 applications of 2500 ppm B-9 SP.

*Branching pattern.*—Spreading and prolific, with 5 to 7 laterals after pinch.

B. Foliage:

*Color (upper surface).*—147A.

*Color (under surface).*—147B.

I claim:

1. A new and distinct Chrysanthemum plant named White Rochelle, as described and illustrated.

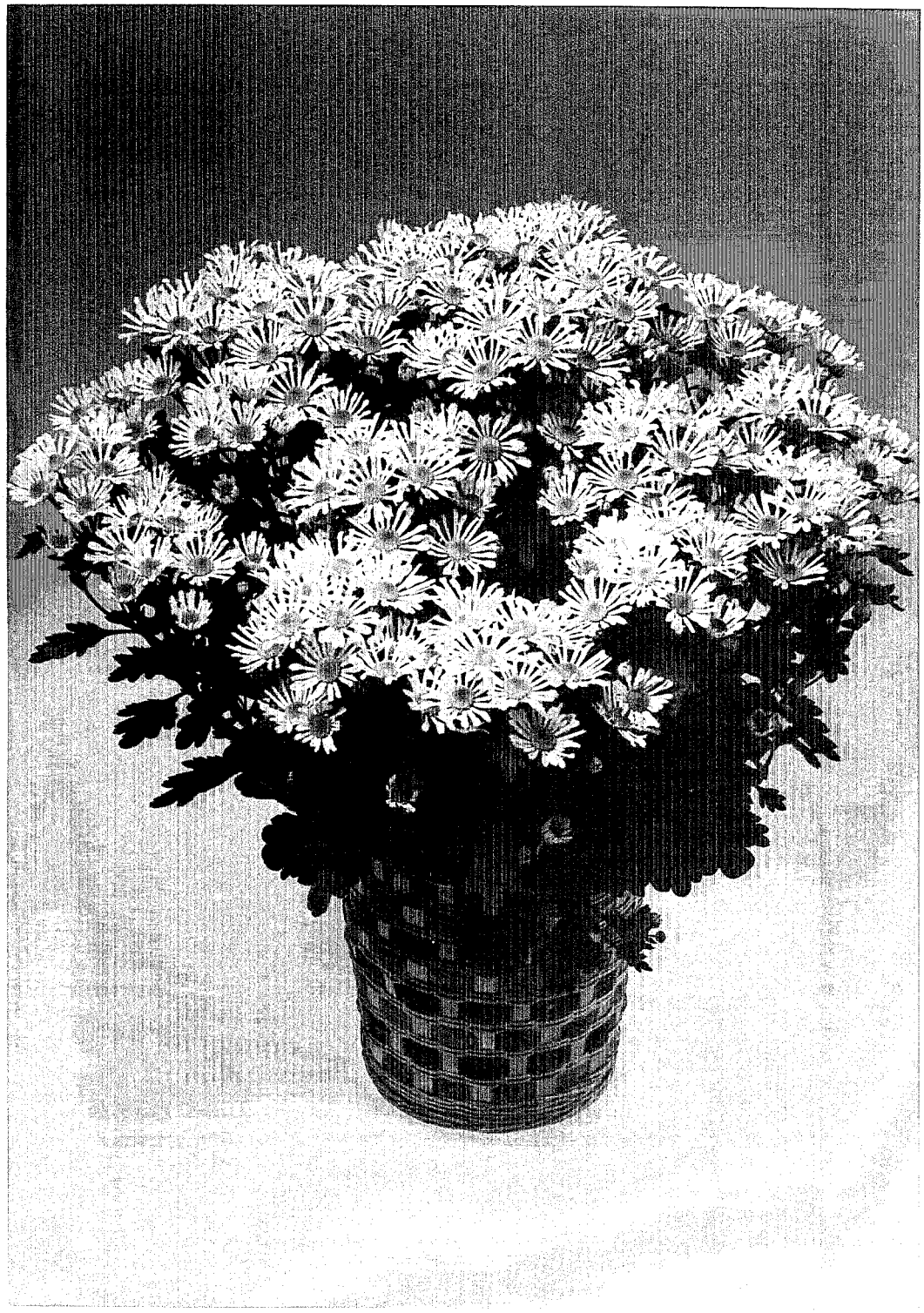

* * * * *